(12) United States Patent
Ong et al.

(10) Patent No.: US 6,979,455 B2
(45) Date of Patent: *Dec. 27, 2005

(54) ANTIMICROBIAL CONCENTRATES

(75) Inventors: Ivan W. Ong, Charlotte, NC (US); Paul Albee, Shamong, NJ (US)

(73) Assignee: Microban Products Company, Huntersville, NC (US)

( * ) Notice: Subject to any disclaimer, the term of this patent is extended or adjusted under 35 U.S.C. 154(b) by 432 days.

This patent is subject to a terminal disclaimer.

(21) Appl. No.: 10/190,947

(22) Filed: Jul. 8, 2002

(65) Prior Publication Data

US 2005/0142200 A1    Jun. 30, 2005

Related U.S. Application Data

(60) Provisional application No. 60/304,242, filed on Jul. 10, 2001.

(51) Int. Cl.$^7$ .......................... A61K 9/10; A01N 25/02; C08K 3/00; C08L 1/00
(52) U.S. Cl. ...................... 424/411; 424/486; 424/487; 514/772; 514/772.1; 514/772.4; 523/122
(58) Field of Search .................. 424/411, 486, 487; 514/772, 772.1, 772.4; 523/122

(56) References Cited

U.S. PATENT DOCUMENTS

| | | | | |
|---|---|---|---|---|
| 5,489,281 A | * | 2/1996 | Watanabe et al. | 604/317 |
| 6,620,474 B1 | * | 9/2003 | Regnier et al. | 428/35.7 |
| 6,653,523 B1 | * | 11/2003 | McCormack et al. | 604/367 |

* cited by examiner

*Primary Examiner*—S. Mark Clardy
(74) *Attorney, Agent, or Firm*—Kennedy Covington Lobdell & Hickman, LLP

(57) ABSTRACT

An antimicrobial concentrate is manufactured from a carrier, one or more antimicrobial agents and optionally one or more modifiers, the carrier having a modified ethylene polymer and optionally an olefin polymer and a method of producing the concentrate by producing the carrier, having the modified ethylene polymer and optionally the olefin polymer, then compounding the carrier with one or more antimicrobial agents and optionally one or more modifiers, to form the concentrate, which does not exhibit chalking and clumping of antimicrobial agent on the surface thereof. An antimicrobial blend that is manufactured from the antimicrobial concentrate, a resin and optionally an additive and a method of producing the blend by combining the concentrate with the resin. An antimicrobial product that is formed by producing a blend, then molding or extruding the blend to form the product, which provides desired antimicrobial efficacy and does not exhibit taste and odor issues associated with food and liquids meant for human consumption, due to leaching of the antimicrobial agent from the surface of the polymeric matrix.

27 Claims, 5 Drawing Sheets

Carrier of Modified Ethylene Polymer and optionally Olefin Polymer + One or More Antimicrobial Agents → Compounding → Antimicrobial Concentrate Combining → Resin Antimicrobial Product ← Molding or Extruding ← Antimicrobial Blend

Polyethylene (PE)

Polypropylene (PP)

FIG. 3 poly (ethylene methyl acrylate) (EMA)

poly (ethylene ethyl acrylate) (EEA)

poly (ethylene vinyl acetate) (EVA)

poly (ethylene carboxylic acid) (ECA)

FIG. 4

2-phenylphenol

2,4,4'-trichloro-2'-hydroxy diphenol ether diiodomethyl-p-tolylsulfone

N-alkyl-N,N-dimethyl-N-benzylammonium chloride zinc 2-mercaptopyridine-N-oxide

FIG. 5

ANTIMICROBIAL CONCENTRATES

CROSS REFERENCE TO RELATED APPLICATION

This application claims the benefit of U.S. Provisional Application No. 60/304,242, filed Jul. 10, 2001.

FIELD OF THE INVENTION

This invention relates generally to an antimicrobial polymer concentrate and a method for producing the antimicrobial concentrate from a carrier having a modified ethylene polymer, and optionally an olefin polymer, with one or more biocidal antimicrobial agents compounded therein. This invention also relates generally to an antimicrobial polymer blend and a method for producing the antimicrobial blend by combining the antimicrobial concentrate with a resin. This invention further relates generally to a method of forming an antimicrobial product from the antimicrobial blend, via molding or extruding.

BACKGROUND OF THE INVENTION

In the past, polyolefin articles exhibiting antimicrobial characteristics have been manufactured by combining a plurality of pellets of a polyolefin antimicrobial composition (composition) with a resin to form a polyolefin antimicrobial mixture (mixture) that is subsequently molded or extruded during manufacture of a polyolefin antimicrobial article (article).

The composition is manufactured by compounding an antimicrobial agent into a polyolefin material (material) having a polyolefin substrate (substrate) of polyethylene (PE), linear low density polyethylene (LLDPE), low density polyethylene (LDPE), high density polyethylene (HDPE), ultra high density polyethylene (UHDPE), or polypropylene (PP).

The resultant composition is combined with a resin to produce the mixture. The material of the composition must be compatible with the resin utilized in the process of making the mixture. A suitable resin may be selected from the group consisting of cellulose plastics, epoxy resins, ethyl cellulose, nylons, polybutylenes, polybutyleneterephthalate, polyethylenes, polyimides, polyphenylene oxide, polypropylenes, styrene butadienes, styrene polymers and copolymers, urethane elastomers, and vinyl polymers and copolymers, or a combination of two or more of these. The mixture may subsequently be molded or extruded during manufacture of the article.

A major disadvantage associated with manufacturing the composition is that the antimicrobial agent, having polar functional group(s), exhibits a low level of compatibility with the substrate of the material. More specifically, functional groups, such as chlorine, iodine, oxygen, hydroxy, sulfone, amine and hydrochloride, of an antimicrobial agent cause the antimicrobial agent to exhibit polar properties. In contrast, the substrate of the material consists of a polyolefin, such as PE, LLDPE, LDPE, HDPE, UHDPE, or PP, having long hydrocarbon chains that are nonpolar in nature. As such, the polar functional groups of the antimicrobial agent are dissimilar, and thus insoluble, or sparingly soluble, with the nonpolar environment created by the long hydrocarbon chains of the substrate of the material. As a result, the antimicrobial agent is insoluble, or sparingly soluble, with the material of the composition.

Phase incompatibility, resulting from the antimicrobial agent being insoluble, or sparingly soluble, with the substrate of the composition may cause gross migration of the antimicrobial agent through the amorphous zones and interstitial regions of the substrate and subsequently to the surface of the substrate. Gross migration of the antimicrobial agent onto the surface of the substrate results in chalking of the antimicrobial agent on the surface of the pellets of the composition as a fine powder. When subjected to elevated temperatures, the fine powder of antimicrobial agent on the surface of the pellets has a tendency to soften and become sticky, resulting in the pellets clumping together. Clumping of the pellets of the composition during processing (i.e., compounding, physical mixing, blending, molding, extruding, packaging and shipping) is undesirable. Additionally, chalking of the composition is aesthetically unpleasing.

Leaching of the antimicrobial agent from the surface of the article, by chemical or mechanical means, may cause taste and odor issues associated with food and liquids meant for human consumption. Additionally, leaching of the antimicrobial agent from the surface of the article may subsequently result in a decrease of longevity of desired antimicrobial efficacy on the surface thereof.

Therefore a need exists for an antimicrobial concentrate that is compatible, or soluble, with the antimicrobial agent. Further needed is an antimicrobial concentrate having an antimicrobial agent that does not exhibit gross migration through the amorphous zones and interstitial regions or the antimicrobial concentrate and subsequently to the surface of the antimicrobial concentrate at high concentrations. Further needed is an antimicrobial concentrate that does not exhibit chalking and clumping of antimicrobial agent on the surface thereof. A need also exists for an antimicrobial product that does not exhibit taste and odor issues associated with food and liquids meant for human consumption, due to leaching of the antimicrobial agent from the surface of the antimicrobial product by chemical or mechanical means. Further needed is an antimicrobial product that does not exhibit a decrease in longevity of desired antimicrobial efficacy.

SUMMARY OF THE INVENTION

The present invention is directed to an antimicrobial concentrate and a method for producing the antimicrobial concentrate from a carrier having a modified ethylene polymer, and optionally an olefin polymer, with one or more antimicrobial agents compounded therein. The present invention is also directed to an antimicrobial blend and a method for producing the antimicrobial blend by combining the antimicrobial concentrate with a resin. The present invention is further directed to a method of forming an antimicrobial product from the antimicrobial blend, via molding or extruding.

The present invention includes an antimicrobial concentrate that is manufactured from a carrier and one or more antimicrobial agents, the carrier having a modified ethylene polymer and optionally an olefin polymer. In addition to the carrier and one or more antimicrobial agents, the antimicrobial concentrate may also include one or more modifiers. The invention also comprehends an antimicrobial blend that is manufactured from an antimicrobial concentrate and a resin. The resin may have an additive incorporated therein.

The present invention comprises a method for producing an antimicrobial concentrate by producing a carrier, having a modified ethylene polymer and optionally an olefin polymer, then compounding the carrier with one or more antimicrobial agents. The method for producing the antimicrobial concentrate may also include compounding one or more modifiers, with the carrier and one or more antimicrobial agents. The present invention also includes a method for producing an antimicrobial blend by first producing an antimicrobial concentrate then combining the antimicrobial concentrate with a resin. The present invention further includes a method of forming an antimicrobial product by producing the antimicrobial blend then molding or extruding the antimicrobial blend to form the antimicrobial product.

An essential feature of the invention is that the antimicrobial agent present within the antimicrobial concentrate has a high degree of compatibility, or solubility, with the modified ethylene polymer of the antimicrobial concentrate. Solubility is a result of the antimicrobial agent and the modified ethylene polymer having functional groups that are similar in polarity. Therefore, by increasing the amount of modified ethylene polymer present within the antimicrobial concentrate, the solubility of the antimicrobial agent within the amorphous zones and interstitial regions of the antimicrobial concentrate are enhanced.

Because the antimicrobial agent has a higher affinity for remaining in solution within the amorphous zones and interstitial regions of the antimicrobial concentrate, gross migration of the antimicrobial agent to the surface of the antimicrobial concentrate at high concentrations is alleviated. As a result, chalking and clumping of the antimicrobial agent on the surface of the antimicrobial concentrate is reduced or substantially eliminated.

Leaching of the antimicrobial agent from the surface of the antimicrobial product by chemical or mechanical means is alleviated. As a result, a number of problems are therefore reduced or substantially eliminated in regards to the antimicrobial product, including taste and odor issues associated with food and liquids meant for human consumption and also loss of desired antimicrobial efficacy on the surface thereof.

BRIEF DESCRIPTION OF THE DRAWINGS

The foregoing and other objects will become more readily apparent by referring to the following detailed description and the appended drawings in which.

DETAILED DESCRIPTION

Figure 1:
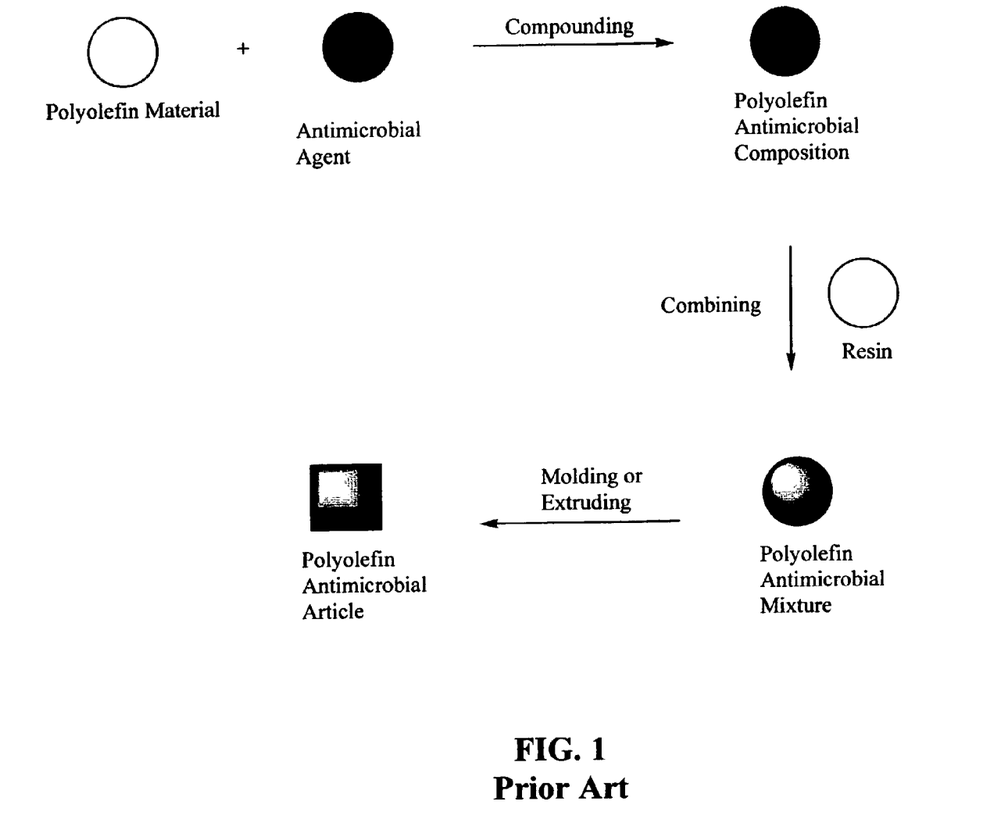
FIG. 1 is a flow chart illustrating the conventional method of manufacturing a polyolefin antimicrobial article.

FIG. 1 illustrates the conventional method of manufacturing a polyolefin antimicrobial article by first compounding an antimicrobial agent into a polyolefin material to produce a polyolefin antimicrobial composition, then combining the polyolefin antimicrobial composition with a resin to produce a polyolefin antimicrobial mixture, followed by molding or extruding the polyolefin antimicrobial mixture to form the polyolefin antimicrobial article.

The present invention is an antimicrobial concentrate and method for producing the antimicrobial concentrate from a carrier having an modified polymer, and optionally an olefin polymer, with one or more antimicrobial agents compounded therein. The present invention is also an antimicrobial blend and method for producing the antimicrobial blend by combining the antimicrobial concentrate with a resin. The present invention is further directed to a method of forming an antimicrobial product from the antimicrobial blend, via molding or extruding.

Figure 2:
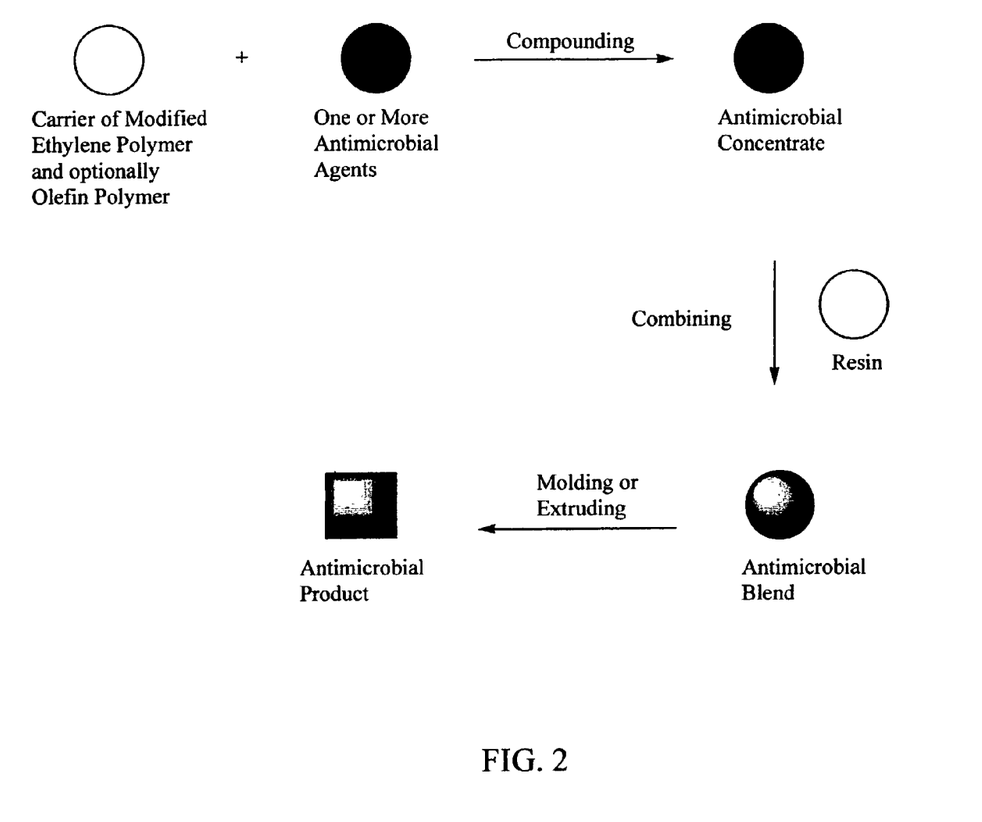
FIG. 2 is a flow chart illustrating a preferred method, in accordance with the present invention, of manufacturing an antimicrobial product.

FIG. 2 illustrates a preferred method, in accordance with the present invention, of manufacturing an antimicrobial product by producing an antimicrobial concentrate by first producing a carrier, having a modified ethylene polymer and optionally an olefin polymer, then compounding the carrier with one or more antimicrobial agents to produce the antimicrobial concentrate, then combining the antimicrobial concentrate with a resin to produce an antimicrobial blend, followed by molding or extruding the antimicrobial blend to form the antimicrobial product. Therefore, the antimicrobial concentrate, the antimicrobial blend, and the antimicrobial product are each composed of a modified polyethylene matrix (matrix).

As shown in FIG. 2, the antimicrobial concentrate (concentrate), in accordance with the present invention, is manufactured by producing a carrier having a modified polymer and optionally an olefin polymer, then compounding the carrier with one or more antimicrobial agents, optionally together with one or more modifiers selected from the group consisting of mineral oil, processing aids, polymerization catalysts, stabilizing aids, fillers, organic colorants, inorganic colorants, dyes, pigments, plasticizers, and environmental protection aids.

Figure 3:
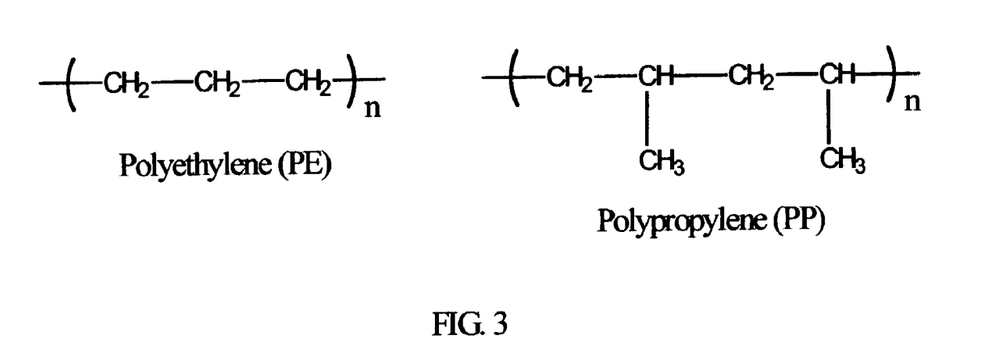
FIG. 3 illustrates chemical structures of the olefin polymer of the carrier.

FIG. 3 illustrates chemical structures of the olefin polymer of the carrier. The olefin polymer of the carrier is selected from the group consisting of PE, LLDPE, LDPE, HDPE, UHDPE, and PP (homopolymer or copolymer).

Figure 4:
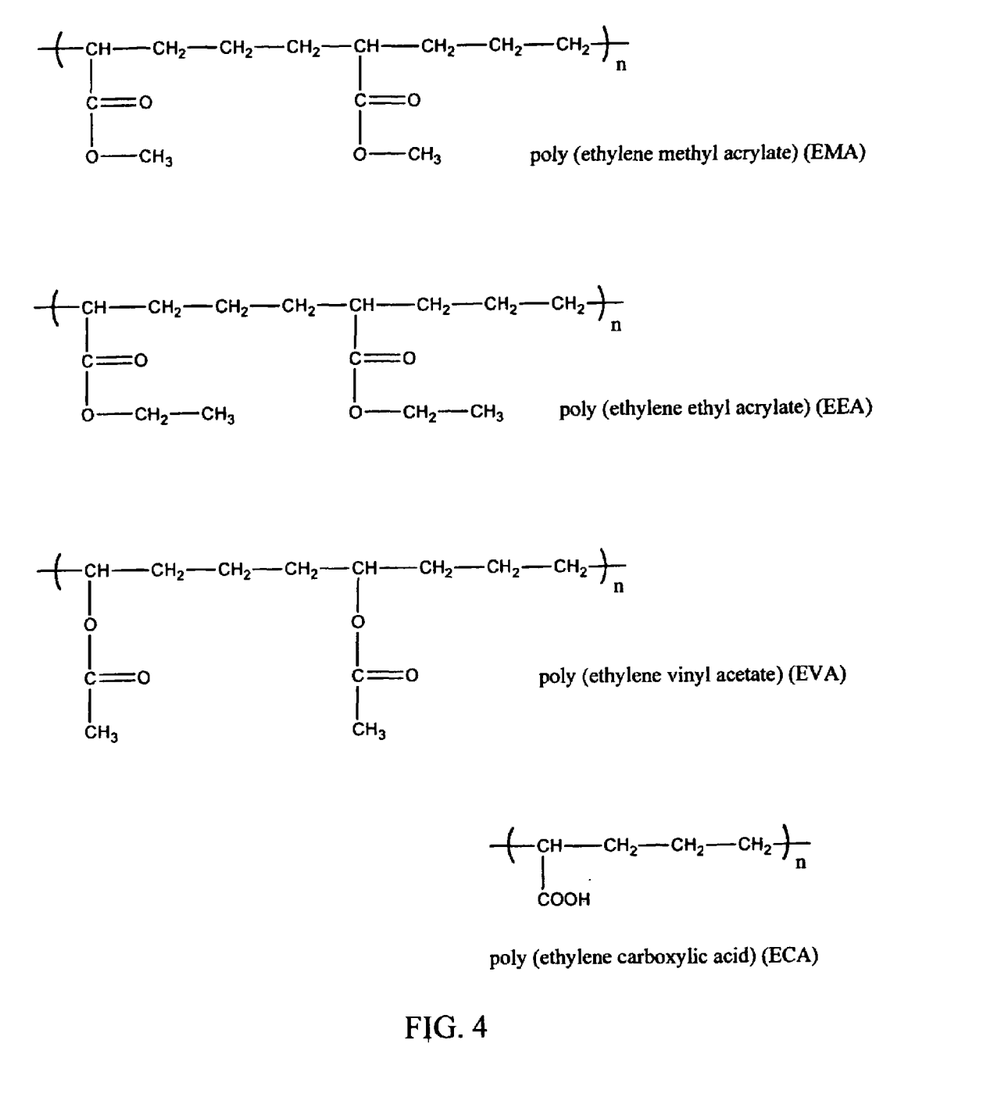
FIG. 4 illustrates chemical structures of the of the modified ethylene polymer of the carrier.

FIG. 4 illustrates some examples of the chemical structures of the of the modified ethylene polymer of the carrier. The modified ethylene polymer of the carrier is selected from the group comprising, but not limited to, Ethylene Vinyl Acetate copolymers (EVA), Ethylene Acrylate copolymers (EMA, EEA), Ethylene Carboxylic Acid copolymers, Ethylene Acrylic Acid, (EAA), Ethylene, Methylene Acrylic Acid (EMAA), Ethylene Polymer based Ionomers (IO), Maleic Anhydride Terpolymers such as Ethylene-n Butyl Acrylate (EnBA).

As also shown in FIG. 2, the resultant concentrate is combined, as an additive, with a suitable resin to produce an antimicrobial blend (blend). The resin may be selected from the group consisting of cellulose plastics, epoxy resins, ethyl cellulose, nylons, polybutylenes, polybutyleneterephthalate, polyethylenes, polyimides, polyphenylene oxide, polypropylenes, styrene butadienes, styrene polymers and copolymers, urethane elastomers, and vinyl polymers and copolymers, or a combination of two or more of these.

As further shown in FIG. 2, the resultant blend is subsequently molded or extruded to form the antimicrobial product (product). The carrier of the concentrate must be compatible with the resin utilized in the process of making the product. The resin may also contain one or more additives selected from the group consisting of processing aids, stabilizing aids, blowing agents, fillers, organic colorants, inorganic colorants, dyes, pigments, plasticizers, and environmental protection aids.

Initially, the antimicrobial agent is compounded into the carrier to produce the concentrate, at appropriate concentrations, typically in the range from about 1 percent to about 25 percent by weight of the concentrate. This concentration range of antimicrobial agent provides safe and effective antimicrobial protection without sacrificing desirable physical properties of the concentrate.

A preferred concentration range of antimicrobial agent within the concentrate is from about 2 percent to about 21.5 percent by weight of the concentrate. A more preferred concentration range of antimicrobial agent within the concentrate is from about 3 percent to about 18 percent by weight of the concentrate. The optimum concentration range of antimicrobial agent within the concentrate is from about 4 percent to about 14.5 percent by weight of the concentrate.

Thereafter, the concentrate is combined, via physical mixing, with the resin to produce the blend, which is subsequently molded or extruded, using conventional plastics manufacturing techniques such as extruding, molding, blow molding, injection molding, rotational molding, thermoforming, etc., to form the product. As a result, the antimicrobial agent concentration initially present within the concentrate is subsequently diluted upon combination with the resin. Therefore, antimicrobial agent is present within the product in appropriate concentrations, typically in the range from about 0.005 percent to about 3 percent by weight of the blend or product. This concentration range of antimicrobial agent is necessary to provide safe and effective antimicrobial protection without sacrificing desirable physical properties of the blend or product.

A preferred concentration range of antimicrobial agent within the blend or product is from about 0.0067 percent to about 2.3 percent by weight of the blend or product. A more preferred concentration range of antimicrobial agent within the blend or product is from about 0.0083 percent to about 1.7 percent by weight of the blend or product. The optimum concentration range of antimicrobial agent within the blend or product is from about 0.01 percent to about 1 percent by weight of the blend or product.

The antimicrobial agent of the present invention is selected from one or more antimicrobial agents that inhibit bacterial, fungal viral and/or other pathogen growth upon contact. Additionally, one or more of the selected antimicrobial agents suppress growth of gram positive bacteria, such as, but not limited to, *Staphylococcus aureus*, gram negative bacteria, such as but not limited to, *Klebsiella pneumoniae*, and fungus, including, but not limited to, yeast, upon contact. By selecting more than one antimicrobial agent, the spectrum of organisms affected by the antimicrobial characteristics of the product is broadened. As a result, antimicrobial efficacy of the product is therefore enhanced.

Figure 5:
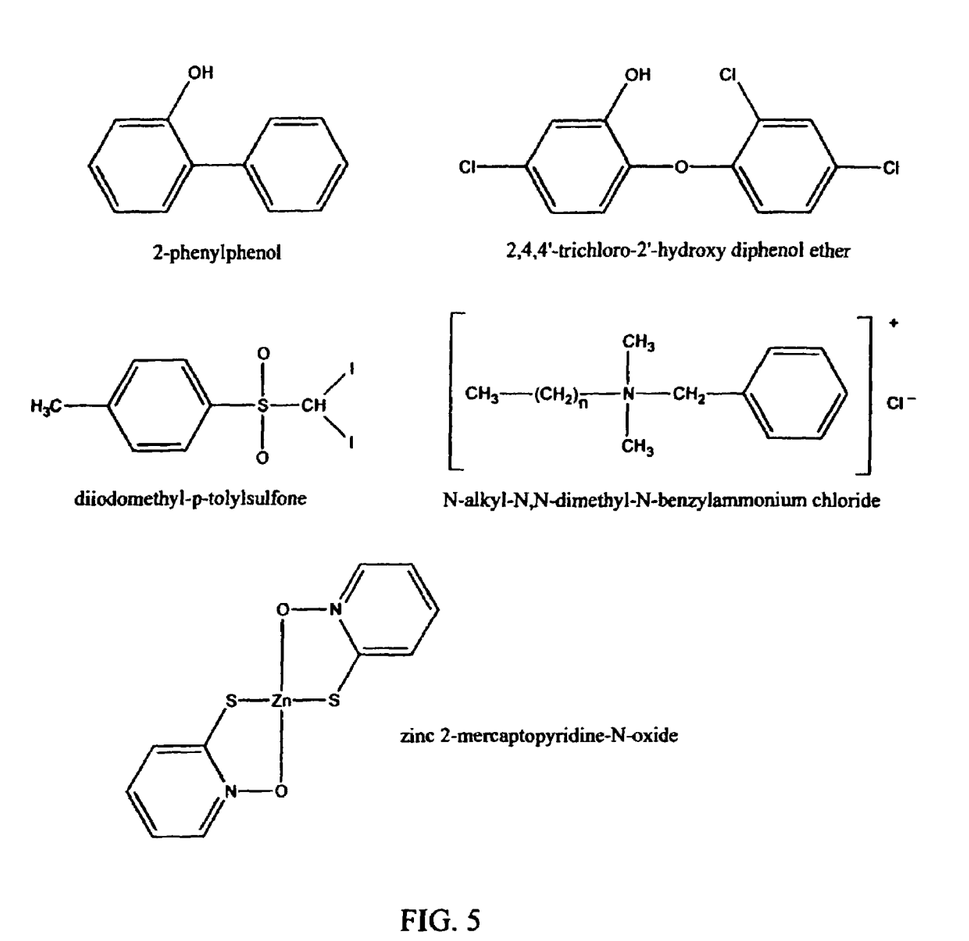
FIG. 5 illustrates chemical structures of the antimicrobial agents.

FIG. 5 illustrates chemical structures of various antimicrobial agents. The antimicrobial agent is one or more antimicrobial agents selected from the group consisting of 2-phenylphenol; 2,4,4'-trichloro-2'-hydroxy diphenol ether; diiodomethyl-4-tolylsulfone; zinc 2-mercaptopyridine-N-oxide; or N-alkyl-N,N-dimethyl-N-benzylammonium chloride. The functional groups, such as chlorine, iodine, oxygen, hydroxy, sulfone, amine, and hydrochloride, of the antimicrobial agent cause the antimicrobial agent to exhibit polar properties.

Fundamentally, solubility is dependent upon the rule that "like dissolves like". Qualitatively, "like" may be defined in terms of similar chemical groups or similar polarities. Therefore, when determining whether one compound is likely to be soluble in another compound, particular attention should be focused on whether the two compounds have similar chemical groups of similar polarity.

The olefin polymer, such as PE, LLDPE, LDPE, HDPE, UHDPE, and PP, of the matrix consists of long hydrocarbon chains that are nonpolar in nature. As such, the polar functional groups of the antimicrobial agent are dissimilar, and thus have a low level of compatibility, with the nonpolar environment created by the long hydrocarbon chains of the olefin polymer of the matrix.

In contrast, the modified ethylene polymer of the matrix is selected from the group consisting of ethylene vinyl alcohols, ethylene vinyl esters, ethylene acrylics, and ethylene acrylates, such as, but not limited to, EVA, ECA, EMA, and EEA, which consist of functional groups, such as alcohol, carboxylic acid, and ester. These functional groups contain electronegative oxygen groups that give rise to polar characteristics along the hydrocarbon backbone of the matrix. As such, the polar functional groups of the antimicrobial agent are similar, and thus exhibit a high level of compatibility, with the polar environment created by the polar functional groups of the modified ethylene polymer of the matrix.

Therefore, an essential feature of the present invention is that the antimicrobial agent and the matrix of the concentrate have functional groups that are similar in polarity. As a result, the antimicrobial agent has an affinity for remaining in solution within the amorphous zones and interstitial regions of the matrix of the concentrate.

If the ratio of the modified ethylene polymer relative to the olefin polymer within the matrix of the concentrate is decreased too much, gross migration of the antimicrobial agent through the amorphous zones and interstitial regions of the concentrate, and subsequently to the surface of the concentrate, results. At high concentrations, the antimicrobial agent exists on the surface of the concentrate as a fine powder, thus creating undesirable chalking and clumping.

An essential feature of the present invention is that the modified ethylene polymer solubilizes the antimicrobial agent within the concentrate, thus tending to cause the antimicrobial agent to remain in solution within the modified ethylene polymer of the matrix. Therefore, by increasing the ratio of the modified ethylene polymer relative to the olefin polymer within the matrix of the concentrate, the antimicrobial agent is deterred from exhibiting gross migration through the amorphous zones and interstitial regions of the matrix. As a result, the concentrate has a lesser amount of antimicrobial agent present on the surface thereof, to exhibit undesirable chalking and clumping.

In accordance with the present invention, the modified ethylene polymer of the carrier of the concentrate is present in an amount from about 10 percent to about 100 percent by weight of the carrier. The carrier of the concentrate optionally has an olefin polymer present in an amount from about 0 percent to about 90 percent by weight of the carrier.

Therefore, by varying the ratio of the modified ethylene polymer relative to the olefin polymer within the matrix of the concentrate, the solubility of the antimicrobial agent within the amorphous zones and interstitial regions of the matrix may be increased or decreased, to prevent undesirable chalking and clumping on the surface of the concentrate.

EXAMPLE 1

To illustrate the reduction of chalking and clumping of the concentrate of the present invention, as opposed to the heavy chalking and clumping associated with the polyolefin antimicrobial composition, four samples were analyzed using ultraviolet spectrometry to determine the relative amount of antimicrobial agent accumulated on the respective surface thereof. The amount of antimicrobial present on the surface of the sample being analyzed correlates to the amount of chalking and clumping associated with that particular sample. More specifically, a high concentration of antimicrobial agent present on the surface of the sample correlates to a higher degree of chalking and clumping associated with that particular sample. Ultraviolet spectrometry was carried out utilizing a high performance liquid chromatograph (HPLC).

The method of evaluating the amount of chalking and clumping associated with each of the four samples is as follows. First, 2.0 g (grams) of the specific sample of composition or concentrate to be analyzed was placed into a test tube containing 4.0 ml (milliliters) of methanol. Second, the test tube was swirled for approximately 10 seconds. During swirling, methanol acts as a solvent and dissolves antimicrobial agent present on the surface of the specific sample to be analyzed. Third, the methanol solution, having antimicrobial agent dissolved therein, was quickly transferred to an HPLC vial and subsequently analyzed, to determine the average amount of antimicrobial agent on the surface of the sample, which is reported in parts per million (ppm).

TABLE 1

| Sample Identification | Antimicrobial Agent on Surface Thereof | Presence of Chalking |
| --- | --- | --- |
| Composition A | 37,688 ppm | Heavy Chalking |
| Concentrate B | 20,744 ppm | Moderate Chalking |

Table 1 shows the ultraviolet spectrometry results for two samples, namely composition A and concentrate B.

Composition A is a polyolefin antimicrobial composition of an antimicrobial agent and a carrier having an olefin polymer. The antimicrobial agent is 2,4,4'-trichloro-2'-hydroxy diphenol ether, which is present at a concentration of about 10 percent by weight of the composition. The olefin polymer is PE, which is present in a concentration of about 90 percent by weight of the composition (i.e., about 99 percent by weight of the polyolefin material).

Concentrate B is a concentrate, of the present invention, that is composed of an antimicrobial agent and a carrier having a modified polymer and an olefin polymer. The antimicrobial agent 2,4,4'-trichloro-2'-hydroxy diphenol ether, which is present in a concentration of about 10 percent by weight of the concentrate. The modified polymer is EMA, which is present in a concentration of about 15 percent by weight of the concentrate (i.e., about 16.7 percent by weight of the carrier). The olefin polymer is PE, which is present in a concentration of about 75 percent by weight of the concentrate (i.e., about 83.3 percent by weight of the carrier).

The aforementioned laboratory test results illustrate the reduction of chalking of the concentrate of the present invention, as opposed to the heavy chalking associated with the polyolefin antimicrobial composition.

TABLE 2

| Sample Identification | Antimicrobial Agent on Surface Thereof | Presence of Chalking |
| --- | --- | --- |
| Composition C | 6,890 ppm | Moderate Chalking |
| Concentrate D | 1,288 ppm | Light Chalking |

Table 2 shows the ultraviolet spectrometry results for two additional samples, namely composition C and concentrate D.

Composition C is a polyolefin antimicrobial composition of an antimicrobial agent and a carrier having an olefin polymer. The antimicrobial agent is 2,4,4'-trichloro-2'-hydroxy diphenol ether, which is present in a concentration of about 10 percent by weight of the composition. The olefin polymer is PP, which is present in a concentration of about 90 percent by weight of the composition (i.e., about 99 percent by weight of the polyolefin material).

Concentrate D is a concentrate, according to the present invention, that is composed of an antimicrobial agent and a carrier having a modified polymer and an olefin polymer. The antimicrobial agent is 2,4,4'-trichloro-2'-hydroxy diphenol ether, which is present in a concentration of about 10 percent by weight of the concentrate. The modified polymer is EMA, which is present in a concentration of about 15 percent by weight of the concentrate (i.e., about 16.7 percent by weight of the carrier). The olefin polymer is PP, which is present in a concentration of about 75 percent by weight of the concentrate (i.e., about 83.3 percent by weight of the carrier).

The aforementioned laboratory test results illustrate the reduction of chalking of the concentrate of the present invention, as opposed to the moderate chalking associated with the polyolefin antimicrobial composition.

EXPERIMENT 1

In order to determine whether the reduced chalking characteristics of the concentrate adversely affected the antimicrobial characteristics of the concentrate, the concentrate of the present invention was tested for antimicrobial efficacy using American Association of Textile Chemists and Colorists Chemists and Colorists Procedures (AATCC) test method 147, or Kirby-Bauer test method, in which, after a predetermined period of time, the zone of inhibition of the organism (i.e., *Staphylococcus aureus* or *Klebsiella pneumoniae*) was measured in millimeters (mm).

TABLE 3

| Sample Identification | Staphylococcus aureus | Klebsiella pneumoniae |
| --- | --- | --- |
| Concentrate E | 15 mm | 15 mm |
| Concentrate F | 13 mm | 14 mm |
| Concentrate G | 15 mm | 15 mm |

Table 3 shows the results of Kirby-Bauer test method (AATCC 147) for three concentrates, namely concentrate E, concentrate F and concentrate G. Concentrate E, concentrate F and concentrate G were each placed in nutrient rich broth containing test organisms, *Staphylococcus aureus* and *Klebsiella pneumoniae*, and subsequently incubated at 37° C.±2° C. for 18 to 24 hours.

Concentrate E is composed of an antimicrobial agent and a carrier having a modified ethylene polymer and an olefin polymer. The antimicrobial agent is 2,4,4'-trichloro-2'-hydroxy diphenol ether, which is present in a concentration of about 10 percent by weight of the concentrate. The modified ethylene polymer is EMA, which is present in a concentration of about 15 percent by weight of the concentrate (i.e., about 16.7 percent by weight of the carrier). The olefin polymer is LDPE, which is present in a concentration of about 75 percent by weight of the concentrate (i.e., about 83.3 percent by weight of the carrier).

Concentrate F is composed of an antimicrobial agent and a carrier having a modified ethylene polymer and an olefin polymer. The antimicrobial agent is 2,4,4'-trichloro-2'-hydroxy diphenol ether, which is present in a concentration of about 10 percent by weight of the concentrate. The modified ethylene polymer is EMA, which is present in a concentration of about 45 percent by weight of the concentrate (i.e., about 50 percent by weight of the carrier). The olefin polymer is LDPE, which is present in a concentration of about 45 percent by weight of the concentrate (i.e., about 50 percent by weight of the carrier).

Concentrate G is composed of an antimicrobial agent and a carrier having a modified ethylene polymer and an olefin polymer. The antimicrobial agent is 2,4,4'-trichloro-2'-hydroxy diphenol ether, which is present in a concentration of about 10 percent by weight of the concentrate. The modified ethylene polymer is EMA, which is present in a concentration of about 15 percent by weight of the concentrate (i.e., about 16.7 percent by weight of the carrier). The olefin polymer is PP, which is present in a concentration of about 75 percent by weight of the concentrate (i.e., about 83.3 percent by weight of the carrier).

The aforementioned laboratory test results illustrate that although the surface of the concentrate is non-chalky in appearance, a sufficient amount of antimicrobial agent, which is incorporated within the matrix of the concentrate, migrates to the surface thereof to exhibit efficacious antimicrobial characteristics.

When producing the blend, which will be molded or extruded to form the product, the operator can calculate the relative ratio of concentrate to resin to be utilized during the step of combining the concentrate with the resin. The relative ratio of concentrate to resin to be utilized is directly dependent upon the concentration of antimicrobial agent already present within the concentrate and the concentration of antimicrobial agent desired within the blend or product. The relative ratio of concentrate to resin to be utilized is also directly dependent upon the ratio of the modified ethylene polymer relative to the olefin polymer desired in the blend or product.

By increasing the ratio of the modified ethylene polymer relative to the olefin polymer within the matrix of the product, the solubility of the antimicrobial agent within the amorphous zones and interstitial regions of the matrix of the product is increased. As a result, the matrix of the product exhibits controlled release, over an extended period of time, of antimicrobial agent through the amorphous zones and interstitial regions of the matrix and subsequently onto the surface of the matrix until a point of equilibrium is reached. As antimicrobial agent is leached from the surface of the matrix, via chemical means (i.e., dissolution within a solvent, fuming, vaporization or volatilization) or mechanical means (i.e., physical abrasion), the equilibrium is disrupted. Disruption in equilibrium stimulates additional controlled release of antimicrobial agent to the surface thereof until equilibrium is reached once again. The amount of antimicrobial agent that migrates to the surface of the matrix of the product is sufficient to provide for desired antimicrobial efficacy on the surface thereof. However, the amount of the antimicrobial agent that leaches from the surface of the product is not enough to cause taste and odor issues associated with food or liquids meant for human consumption. Furthermore, the amount of the antimicrobial agent that leaches from the surface of the product is not enough to cause a decrease in antimicrobial longevity of desired antimicrobial efficacy of the product.

EXAMPLE 2

To illustrate the absence of taste and odor issues associated with food and liquids meant for human consumption that were in intimate contact with an antimicrobial product manufactured from the concentrate of the present invention, as opposed to the presence of taste and odor issues associated with food and liquids meant for human consumption that were in intimate contact with an antimicrobial article manufactured from a polyolefin antimicrobial composition, two samples underwent blind taste and odor tests. The procedure for performing the taste and odor tests initially involved placing 1000 ml of distilled water into the specific sample to be tested and subsequently allowing the water to remain in intimate contact therewith for a period of 72 hours at approximately 90° C. Blind taste and odor tests were then performed on the water previously contained within each of the two respective samples.

TABLE 4

| Sample Identification | Average Percentage of Respondents Indicating a Presence of Taste or Odor Issues |
| --- | --- |
| Article A | 100% (Failed) |
| Product B | 30% (Passed) |

Table 4 shows the blind taste and odor test results for two products, namely article A and product B.

Polyolefin antimicrobial article A is composed of a polyolefin antimicrobial mixture molded into the shape of a reservoir receptacle. The resin is HDPE and is present within the mixture in a concentration of about 97.5 percent by weight of the mixture. The polyolefin antimicrobial composition is present within the mixture in a concentration of about 2.5 percent by weight of the mixture. The composition is composed of an antimicrobial agent and a polyolefin material. The antimicrobial agent of the composition is 2,4,4'-trichloro-2'-hydroxy diphenol ether, which is present in a concentration of about 10 percent by weight of the composition. The material of the composition is PP, which is present in a concentration of about 90 percent by weight of the composition (i.e., about 99 percent by weight of the material).

Product B is an antimicrobial blend molded into the shape of a reservoir receptacle. The resin is HDPE and is present within the blend in a concentration of about 97.5 percent by weight of the blend. The antimicrobial concentrate is present within the blend in a concentration of about 2.5 percent by weight of the blend. The concentrate is composed of an antimicrobial agent and a carrier having a modified ethylene polymer. The antimicrobial agent of the concentrate is 2,4,4-trichloro-2'-hydroxy diphenol ether, which is present at a concentration of about 10 percent by weight of the concentrate. The modified ethylene polymer of the concentrate is EMA, which is present in a concentration of about 90 percent by weight of the concentrate (i.e., about 99 percent by weight of the carrier).

The aforementioned test results illustrate that product B, which was manufactured from the concentrate of the present invention, passed the blind taste and odor tests, unlike article A, which was manufactured from the polyolefin antimicrobial composition.

EXAMPLE 3

To illustrate antimicrobial efficacy, the product that was manufactured from the concentrate of the present invention, was tested for antimicrobial efficacy using American Association of Textile Chemists and Colorists Chemists and Colorists Procedures (AATCC) test method 147, or Kirby-Bauer test method, in which, after a predetermined period of time, the zone of inhibition of the organism (i.e., *Staphylococcus aureus* or *Klebsiella pneumoniae*) was measured in millimeters (mm).

TABLE 5

| Sample Identification | Staphylococcus aureus | Klebsiella pneumoniae |
| --- | --- | --- |
| Product C | 16 mm | 15 mm |
| Product D | 17 mm | 16 mm |

Table 5 shows the results of Kirby-Bauer test method (AATCC 147) for two products, namely product C and product D. Product C and product D were each placed in nutrient rich broth containing test organisms, *Staphylococcus aureus* and *Klebsiella pneumoniae*, and subsequently incubated at 37° C. ±2° C. for 18 to 24 hours.

Product C is a blend of a concentrate and a resin. The concentrate is composed of an antimicrobial agent and a carrier having a modified ethylene polymer and an olefin polymer. The antimicrobial agent of the concentrate is 2,4,4'-trichloro-2'-hydroxy diphenol ether, which is present in a concentration of about 10 percent by weight of the concentrate. The modified ethylene polymer of the concentrate is EMA, which is present in a concentration of about 15 percent by weight of the concentrate (i.e., about 16.7 percent by weight of the carrier). The olefin polymer of the concentrate is HDPE, which is present in a concentration of about 75 percent by weight of the concentrate (i.e., about 83.3 percent by weight of the carrier). The resin is HDPE, which is present at a concentration of about 98.75 percent by weight of Product C. Therefore, the concentrate is present at a concentration of about 1.25 percent by weight of Product C. As a result, the antimicroibal agent (2,4,4'-trichloro-2'-hydroxy diphenol ether) of the concentrate, is present at a diluted concentration of about 0.125 percent by weight of Product C.

Product D is of a blend of a concentrate and a resin. The concentrate is composed of an antimicrobial agent and a carrier having a modified ethylene polymer and an olefin polymer. The antimicrobial agent of the concentrate is 2,4,4'-trichloro-2'-hydroxy diphenol ether, which is present at a concentration of about 10 percent by weight of the concentrate. The modified ethylene polymer of the concentrate is EMA, which is present in a concentration of about 15 percent by weight of the concentrate (i.e., about 16.7 percent by weight of the carrier). The olefin polymer of the concentrate is HDPE, which is present at a concentration of about 75 percent by weight of the concentrate (i.e., about 83.3 percent by weight of the carrier). The resin is HDPE, which is present in a concentration of about 97.5 percent by weight of Product D. Therefore, the concentrate is present in a concentration of about 2.5 percent by weight of Product D. As a result, the antimicrobial agent (2,4,4'-trichloro-2'-hydroxy diphenol ether) of the concentrate, is present in a diluted concentration of about 0.25 percent by weight of Product D.

The aforementioned laboratory test results illustrate that the antimicrobial characteristics of products, manufactured from the concentrates of the present invention, are very efficacious. Based on the results, products, manufactured from the concentrates of the present invention, minimize microbial contamination via self-sustained self-sterilization by controlled release of an effective and desired amount of antimicrobial agent for an extended period of time.

Products manufactured from the concentrates of the present invention, as herein described, may include, but are not limited to, fibers and films. Products manufactured from the concentrates of the present invention that are made for particular applications involving contact with food or liquids meant for human consumption, may include, but are not limited to, plastic cutting boards, plastic counter tops, plastic table covers, plastic place mats, plastic refrigerator components, plastic microwave components, plastic plates and bowls, plastic utensils, plastic straws, plastic carry-out or left over to-go containers for food, plastic food wrappers, plastic sealable containers, plastic sealable bags, plastic bottles and plastic bottle caps for beverage containers, plastic water filter components, plastic water softener components, plastic water piping, and plastic spouts intimately associated with beverages such as coffee.

From the foregoing, it is clear that the present invention provides an antimicrobial concentrate that is compatible, or soluble, with the antimicrobial agent. The present invention also provides an antimicrobial concentrate having an antimicrobial agent that does not exhibit gross migration through the amorphous zones and interstitial regions of the antimicrobial concentrate and subsequently to the surface of the concentrate at high concentrations. The present invention also provides an antimicrobial concentrate that does not exhibit chalking and clumping of antimicrobial agent on the surface thereof. The present invention also provides an antimicrobial product that does not exhibit taste and odor issues associated with food and liquids meant for human consumption, due to leaching of the antimicrobial agent from the surface of the product. The present invention also provides an antimicrobial product that exhibits controlled release of antimicrobial agent over an extended period of time thus increasing longevity of desired antimicrobial efficacy of the product.

It is to be clearly understood that the foregoing description and specific embodiments are merely illustrative of the best mode of the present invention and the principles thereof and are not intended as limitations on the scope of the invention, and therefore various modifications and additions may be made to the structures, compounds, compositions, and methods described herein by those skilled in the art, without departing substantially from the essential concepts, spirit, and scope of the invention.

What is claimed is:

1. A method for producing an antimicrobial concentrate, comprising the steps of:
    (A) producing a carrier comprising:
        (1) a modified ethylene polymer; and
        (2) optionally an olefin polymer; and
    (B) compounding said carrier with an antimicrobial agent to produce said antimicrobial concentrate.

2. A method for producing an antimicrobial concentrate according to claim 1, wherein said compounding step further comprises compounding a modifier with said carrier and said antimicrobial agent.

3. An antimicrobial concentrate comprising:
    (A) a carrier, comprising:
        (1) a modified ethylene polymer; and
        (2) optionally an olefin polymer; and
    (B) an antimicrobial agent.

4. An antimicrobial concentrate according to claim 3, wherein said antimicrobial concentrate further comprises a modifier.

5. The antimicrobial concentrate according to claim 3, wherein said modified ethylene polymer of said carrier is selected from the group consisting of ethylene vinyl alcohols, ethylene vinyl acetate copolymers, ethylene ethyl acrylate copolymers, ethylene butyl acrylate copolymers, ethylene carboxylic acid copolymers, ethylene acrylic acid, ethylene methylene acrylic acid, ethylene polymer based ionomers, maleic anhydride terpolymers, ethylene vinyl esters, ethylene acrylics, and ethylene acrylates.

6. An antimicrobial concentrate according to claim 3, wherein said olefin polymer of said carrier is selected from the group consisting of PE, LLDPE, LDPE, HDPE, UHDPE, and PP.

7. An antimicrobial concentrate according to claim 3, wherein said antimicrobial agent is selected from the group consisting of 2-phenylphenol; 2,4,4'-trichloro-2'-hydroxy diphenol ether; diiodomethyl-4-tolylsulfone; zinc 2-mercaptopyridine-N-oxide; and N-alkyl-N,N-dimethyl-N-benzylammonium chloride, or a combination of two or more of these.

8. An antimicrobial concentrate according to claim 4, wherein said modifier is selected from the group consisting of mineral oil, processing aids, polymerization catalysts, stabilizing aids, fillers, organic colorants, inorganic colorants, dyes, pigments, plasticizers, and environmental protection aids, or a combination of two or more of these.

9. An antimicrobial concentrate according to claim 3, wherein said antimicrobial agent is incorporated into said carrier in an amount from about 1 percent to about 25 percent by weight of said antimicrobial concentrate.

10. An antimicrobial concentrate according to claim 3, wherein said modified ethylene polymer of said carrier is present in an amount from about 10 percent to about 100 percent by weight of said carrier.

11. An antimicrobial concentrate according to claim 3, wherein said olefin polymer of said carrier is present in an amount from about 0 percent to about 90 percent by weight of said carrier.

12. A method for producing an antimicrobial blend, comprising the steps of:
(A) producing an antimicrobial concentrate comprising the steps of:
(1) producing a carrier comprising:
(a) a modified ethylene polymer; and
(b) optionally an olefin polymer; and
(2) compounding said carrier with an antimicrobial agent to produce said antimicrobial concentrate; and
(B) combining said antimicrobial concentrate with a resin to produce said antimicrobial blend.

13. A method for producing an antimicrobial blend according to claim 12, wherein said compounding step further comprises compounding a modifier with said carrier and said antimicrobial agent.

14. An antimicrobial blend comprising:
(A) an antimicrobial concentrate comprising:
(1) a carrier, comprising:
(a) a modified ethylene polymer; and
(b) optionally an olefin polymer; and
(2) an antimicrobial agent; and
(B) a resin.

15. An antimicrobial blend according to claim 14, further comprising a modifier.

16. An antimicrobial blend according to claim 14, wherein said resin further comprises an additive incorporated therein.

17. The antimicrobial blend according to claim 14, wherein said modified ethylene polymer of said carrier is selected from the group consisting of ethylene vinyl alcohols, ethylene vinyl acetate copolymers, ethylene ethyl acrylate copolymers, ethylene butyl acrylate copolymers, ethylene carboxylic acid copolymers, ethylene acrylic acid, ethylene methylene acrylic acid, ethylene polymer based ionomers, maleic anhydride terpolymers, ethylene vinyl esters, ethylene acrylics, and ethylene acrylates.

18. An antimicrobial blend according to claim 14, wherein said olefin polymer of said carrier is selected from the group consisting of PE, LLDPE, LDPE, HDPE, UHDPE, and PP.

19. An antimicrobial blend according to claim 14, wherein said antimicrobial agent is selected from the group consisting of 2-phenylphenol; 2,4,4'-trichloro-2'-hydroxy diphenol ether; diiodomethyl-4-tolylsulfone; zinc-2-mercaptopyridine-N-oxide; and N-alkyl-N,N-dimethyl-N-benzylammonium chloride, or a combination of two or more of these.

20. An antimicrobial blend according to claim 14, wherein said resin is selected from the group consisting of cellulose plastics, epoxy resins, ethyl cellulose, nylons, polybutylenes, polybutyleneterephthalate, polyethylenes, polyimides, polyphenylene oxide, polypropylenes, styrene butadienes, styrene polymers and copolymers, urethane elastomers, and vinyl polymers and copolymers, or a combination of two or more of these.

21. An antimicrobial blend according to claim 15, wherein said modifier is selected from the group consisting of mineral oil, processing aids, polymerization catalysts, stabilizing aids, fillers, organic colorants, inorganic colorants, dyes, pigments, plasticizers and environmental protection aids, or a combination of two or more of these.

22. An antimicrobial blend according to claim 16, wherein said additive is selected from the group consisting of processing aids, stabilizing aids, blowing agents, fillers, organic colorants, inorganic colorants, dyes, pigments, plasticizers and environmental protection aids, or a combination of two or more of these.

23. An antimicrobial blend according to claim 14, wherein said antimicrobial agent is incorporated into said antimicrobial blend in an amount from about 0.005 percent to about 3 percent by weight of said antimicrobial blend.

24. A method for forming an antimicrobial product, comprising the steps of:
(A) producing an antimicrobial concentrate comprising the steps of:
(1) producing a carrier comprising:
(a) a modified ethylene polymer; and
(b) optionally an olefin polymer; and
(2) compounding said carrier with an antimicrobial agent to produce said antimicrobial concentrate; and
(B) combining said antimicrobial concentrate with a resin to produce said antimicrobial blend; and
(C) molding or extruding said antimicrobial blend to form said antimicrobial product; wherein said product is utilized for making fibers and films and for applications involving contact with foods or liquids meant for human consumption.

25. The antimicrobial concentrate according to claim 3, wherein said modified ethylene polymer of said carrier is ethylene methyl acrylate.

26. The antimicrobial concentrate according to claim 14, wherein said modified ethylene polymer of said carrier is ethylene methyl acrylate.

27. The method of forming an antimicrobial product according to claim 24, wherein the application involving contact with foods or liquids meant for human consumption is selected from the group consisting of plastic cutting boards, plastic counter tops, plastic table covers, plastic place mats, plastic refrigerator components, plastic microwave components, plastic plates and bowls, plastic utensils, plastic straws, plastic carry-out or left over to-go containers for food, plastic food wrappers, plastic sealable containers, plastic sealable bags, plastic bottles, plastic bottle caps for beverage containers, plastic water filter components, plastic water softener components, plastic water piping, and plastic spouts.

* * * * *